US006546794B2

(12) United States Patent
Kim et al.

(10) Patent No.: US 6,546,794 B2
(45) Date of Patent: Apr. 15, 2003

(54) LIQUID LEVEL MEASURING APPARATUS AND METHOD

(75) Inventors: Yong-geun Kim, Gyeonggi-do (KR);
Jin-soo Lee, Gyeonggi-do (KR);
Kwang-taek Lim, Gyeonggi-do (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 09/942,969

(22) Filed: Aug. 31, 2001

(65) Prior Publication Data

US 2002/0129649 A1 Sep. 19, 2002

(30) Foreign Application Priority Data

Mar. 10, 2001 (KR) ......................... 2001-12443

(51) Int. Cl.[7] .............. G01F 23/00; G01H 5/00
(52) U.S. Cl. ................... 73/290 V; 73/597
(58) Field of Search .............. 73/290 V, 290 R, 73/597; 324/124, 92

(56) References Cited

U.S. PATENT DOCUMENTS

| | | | | |
|---|---|---|---|---|
| 4,095,475 A | * | 6/1978 | Buckley ............... 73/290 R |
| 4,107,993 A | * | 8/1978 | Shuff et al. ............... 73/290 R |
| 5,136,884 A | * | 8/1992 | Lovett ............... 73/313 |
| 5,365,178 A | * | 11/1994 | Van Der Pol ............... 324/644 |
| 5,689,265 A | * | 11/1997 | Otto et al. ............... 342/124 |
| 5,851,083 A | * | 12/1998 | Palan ............... 403/337 |
| 5,948,979 A | * | 9/1999 | Fitsch et al. ............... 73/290 V |
| 6,128,967 A | * | 10/2000 | Campbell ............... 73/866.5 |
| 6,166,681 A | * | 12/2000 | Meszaros et al. ............ 342/124 |
| 6,295,018 B1 | * | 9/2001 | Diede et al. ............... 342/124 |

\* cited by examiner

*Primary Examiner*—Daniel S. Larkin
*Assistant Examiner*—K Wilson
(74) *Attorney, Agent, or Firm*—Sughrue Mion, PLLC

(57) ABSTRACT

An apparatus and method for measuring a liquid level in a vessel using an acoustic wave. Acoustic tubes have first ends disposed vertically along a sidewall of the vessel for each of the liquid levels to be measured, and the tubes communicate with the inside of the vessel. Second ends of the tubes are connected to a common tube. A storage level sensor board generates the acoustic wave in the vessel, receives the acoustic wave propagated through the acoustic tubes and the common tube, and determines the level of liquid in the vessel based on the received acoustic wave.

13 Claims, 5 Drawing Sheets

US 6,546,794 B2

LIQUID LEVEL MEASURING APPARATUS AND METHOD

BACKGROUND OF THE INVENTION

1. Field of the Invention

The present invention relates to an apparatus and method for measuring a liquid level using acoustic waves.

2. Description of the Related Art

Referring to FIG. 1, a conventional liquid level gauge includes a vessel 100 containing a predetermined amount of liquid 105. An optical sensor is included, comprised of a light-emitting portion 110 for emitting light, and a light-receiving portion 113 that receives the light emitted from the light emitting portion 110, and determines an amount of transmission, both of which are disposed at sidewalls of the vessel 100. The amount of transmission received by light receiving portion 113 indicates the quantity of the liquid 105 in vessel 100. Liquid 105 is supplied to and withdrawn from the vessel 100 by inlet 115 and outlet 118, respectively.

The optical sensor described above measures the level of liquid 105 by detecting an amount of light either reflected from the vessel 100, or transmitted into the liquid 105, after being radiated from the light emitting portion 110. However, this approach may require additional optical sensors for accurate liquid level measurement, since a liquid level can be measured only when the liquid 105 is filled up at least to the level at which the light emitting portion 110 and the light receiving portion 113 are mounted. For example, as shown in FIG. 1, if the height of the liquid 105 is L, which is less than that the height of the light emitting portion 110 and the light receiving portion 113, a liquid level measurement cannot be made. Thus, this approach restricts the liquid level measurement range, and would require additional cost if the measurement range were to be increased due to the need to add additional optical sensors. Furthermore, this approach is limited in its applications since the liquid must be sufficiently transparent for light to be transmitted.

If the conventional liquid level gauge is used in a printer, an error may occur in measuring the storage level of the liquid 105 since solidified ink may remain on an inner wall of the vessel 100 when the ink fills the vessel 100 and flows into the inlet 115 or out of the outlet 118.

SUMMARY OF THE INVENTION

To solve the above problems, it is an objective of the present invention to provide an apparatus and method for measuring a liquid level using acoustic waves that can precisely measure a liquid level without restrictions on the type of liquid, e.g., whether the liquid is transparent or opaque.

Accordingly, the present invention provides an apparatus for measuring a liquid level including: a vessel containing a liquid; a plurality of acoustic tubes having first ends disposed vertically along a sidewall of the vessel for each of liquid levels to be measured and connected to the inside of the vessel, and second ends connected to a common tube; and a storage level sensor board that generates an acoustic wave in the vessel, receives an acoustic wave propagated through one or more of the acoustic tubes and the common tube, and determines the level of liquid in the vessel based on the received acoustic wave.

Preferably, the storage level sensor board includes: an acoustic generator that generates an acoustic wave of predetermined frequency; a speaker that transmits the acoustic wave generated by the acoustic generator into the vessel; an acoustic sensor that detects the acoustic wave propagated through one or more of the plurality of acoustic tubes; an analog-to-digital converter that digitalizes a signal output from the acoustic sensor; and a data processor that evaluates a liquid level from data output from the analog-to-digital converter. Preferably, the storage level sensor board further includes a barrier wall disposed adjacent to the plurality of acoustic tubes, and supported at an upper surface of the vessel so that the barrier wall may be separated from the bottom of the vessel by a predetermined distance. Furthermore, it is preferable that the speaker is disposed between the barrier wall and the sidewall of the vessel at which the plurality of acoustic tubes are disposed.

The present invention also provides a method of measuring a liquid level including the steps of: generating an acoustic wave in a vessel containing a liquid; arranging a plurality of acoustic tubes disposed vertically along a sidewall of the vessel, and receiving an acoustic wave propagated through one or more acoustic tubes which are not submerged in the liquid; and outputting the received acoustic wave as an electrical signal, comparing the output electrical signal with tabulated data and evaluating a liquid level.

BRIEF DESCRIPTION OF THE DRAWINGS

The above objectives and advantages of the present invention will become more apparent by describing in detail preferred embodiments thereof with reference to the attached drawings in which.

DETAILED DESCRIPTION OF THE PREFERRED EMBODIMENTS

Figure 1:
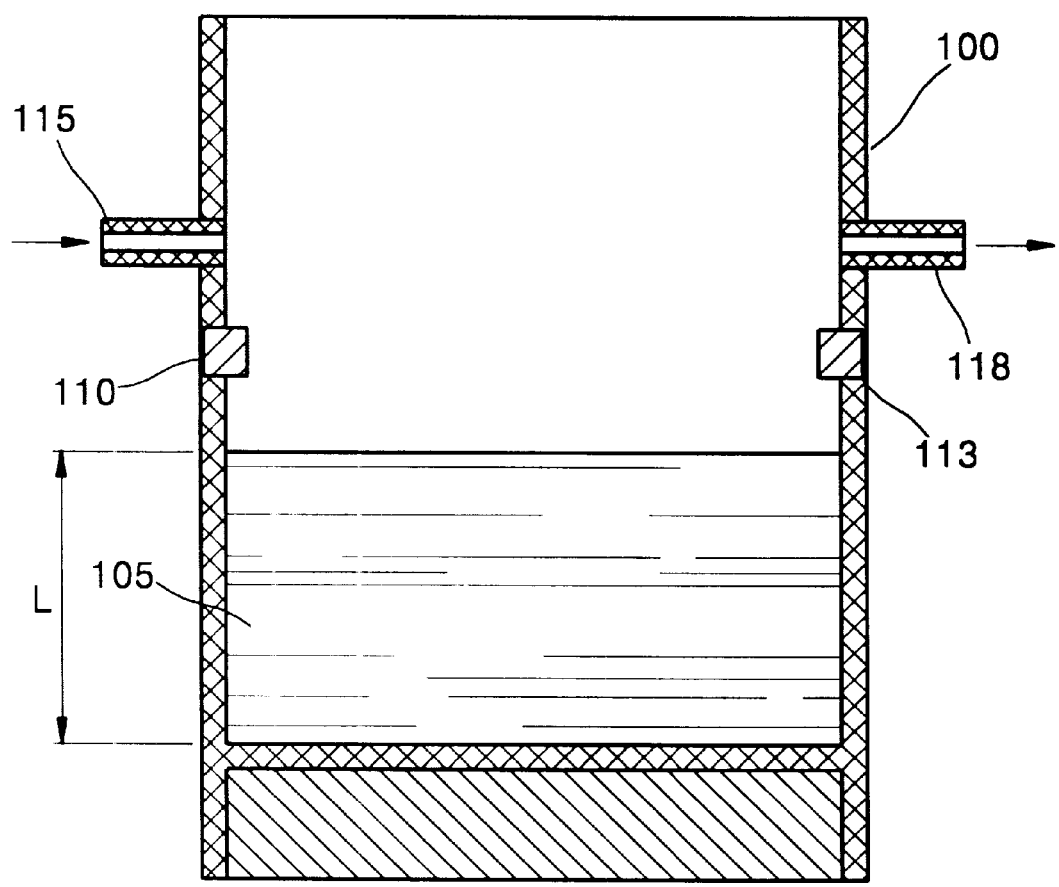
FIG. 1 shows a conventional liquid level gauge.
Figure 2:
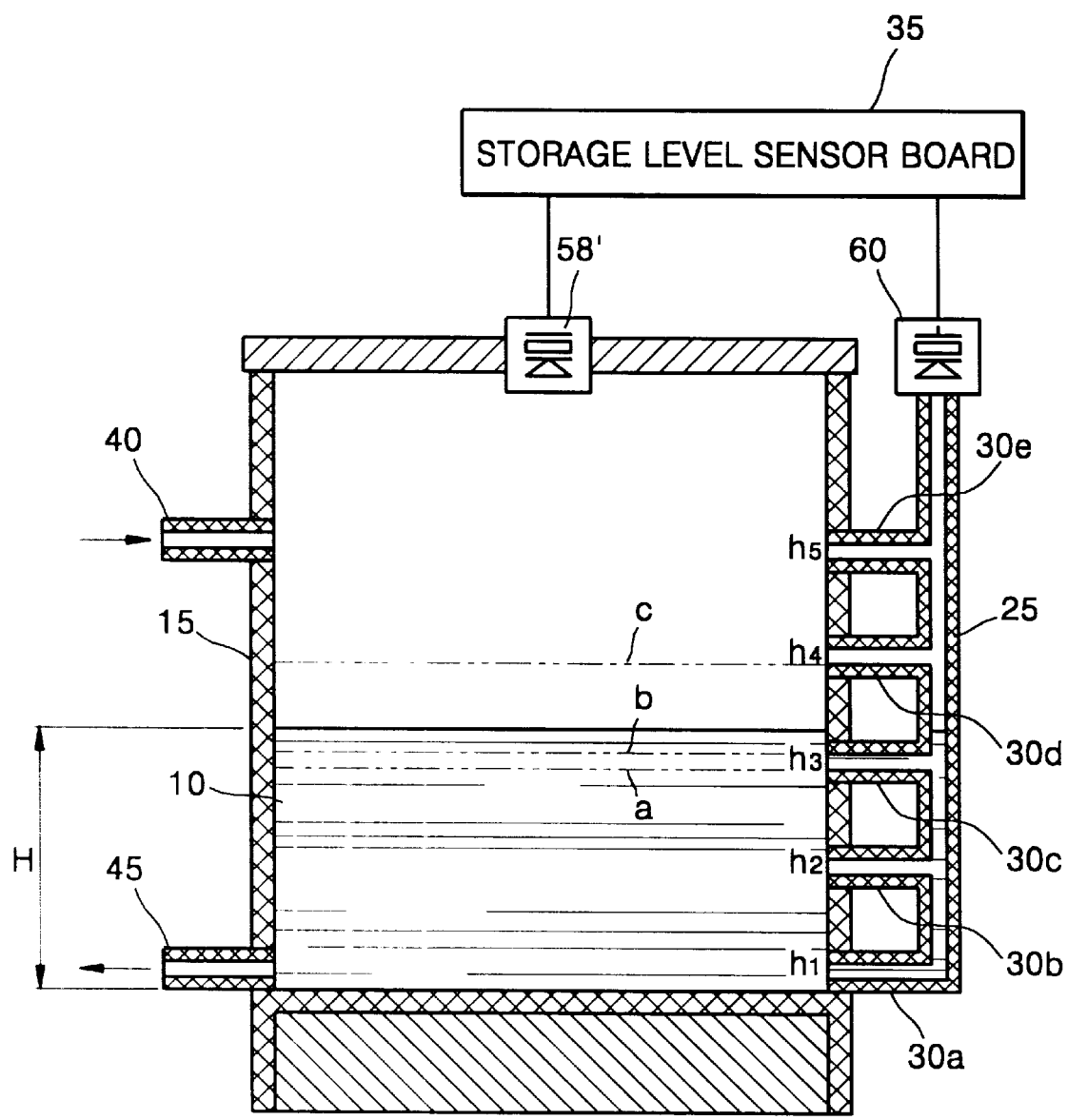
FIG. 2 is a schematic diagram of a liquid level gauge according to an embodiment of the present invention.

FIG. 2 shows a liquid level gauge according to an embodiment of the present invention, including a storage vessel 15 containing liquid 10, a plurality of acoustic tubes 30a, 30b, 30c, 30d, and 30e disposed vertically along a sidewall of the storage vessel 15 at regular intervals, and a storage level sensor board 35. The sensor board 35 generates an acoustic wave in the storage vessel 15, and receives an acoustic wave that has either passed through a volume of liquid 10, or a volume of the vessel with no liquid present, in order to measure the level of the liquid 10. Inlet 40 and outlet 45 respectively supply and withdraw liquid 10 from the storage vessel 15.

Each of the plurality of acoustic tubes 30a, 30b, 30c, 30d, and 30e are disposed vertically along the sidewall of the storage vessel 15 for each storage level of the liquid 10 to be measured. One end of each of the acoustic tubes 30a, 30b, 30c, 30d, and 30e is connected to the storage vessel 15 and the other end is connected to a common tube 25. Thus, the plurality of acoustic tubes 30a, 30b, 30c, 30d, and 30e are connected to each other. A speaker 58 is provided to transmit an acoustic wave into the storage vessel 15, and an acoustic sensor 60 for detecting the acoustic wave is disposed at one end of the common tube 25 to receive the acoustic wave transmitted from some of the acoustic tubes 30a, 30b, 30c, 30d, and 30e. The speaker 58 may generate, for example, acoustic waves or ultrasonic waves.

In this embodiment, acoustic tubes 30a, 30b, 30c, 30d, and 30e are disposed vertically from the bottom of the storage vessel 15 upward and have heights h1, h2, h3, h4, and h5, respectively. The height of the liquid 10 from the bottom of the storage vessel 15 is H. In this case, the interior of the storage vessel 15 is divided into two regions depending on presence of the liquid 10, one part filled with the liquid 10, and the other part containing no liquid. When transmitted, the acoustic wave is reflected or refracted at the surface of the liquid 10 thereby significantly preventing propagation of the acoustic wave into the part filled with the liquid 10 and through the acoustic tubes 30a, 30b, and 30c, which are located below the surface of the liquid 10. Conversely, an acoustic wave freely travels in the part containing no liquid to reach the acoustic sensor 60 through the acoustic tubes 30d and 30e.

The acoustic wave propagates through the acoustic tubes 30d and 30e containing no liquid 10, and the amount of acoustic waves vary depending on the number of the acoustic tubes through which the acoustic wave propagates. The storage level sensor board 35 converts the received acoustic wave from sensor 60 into an electrical signal and then outputs the signal.

Figure 3:
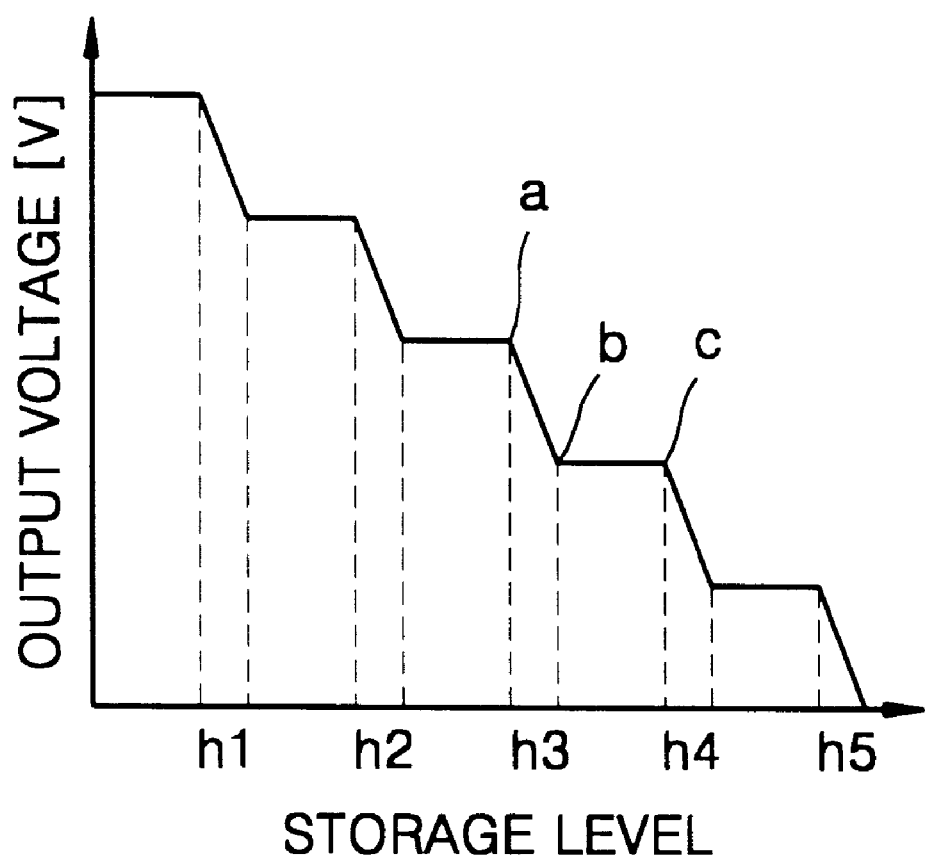
FIG. 3 is a graph of an output voltage with respect to changes in a storage level as a result of measuring a liquid level using a liquid level gauge according to the present invention.

FIG. 3 is a graph showing a voltage output, obtained by converting the acoustic wave received by the acoustic sensor 60 into an electrical signal, versus the storage level of the liquid 10. As is evident from this graph, the output voltage becomes lower as the storage level of the liquid 10 becomes higher. For example, when the level of the liquid 10 is below the third acoustic tube 30c, an acoustic wave propagates to the acoustic sensor 60 through three acoustic tubes 30c, 30d, and 30e. The output voltage generated when the acoustic wave propagates to the acoustic sensor 60 is represented by point a on the graph of FIG. 3. Then, as the height of the liquid 10 is increased to fill up the third acoustic tube 30c, the output voltage generated when the acoustic wave reaches the acoustic sensor 60 decreases to point b on the graph of FIG. 3. The point b represents a point in time when the liquid entirely submerges the third acoustic tube 30c. Then, since an acoustic wave continues to propagate through the two acoustic tubes 30d and 30e until the liquid 10 reaches the fourth acoustic tube 30d, the output voltage remains the same during an interval from point b to point c. That is, since the path through which the acoustic wave propagates is not affected when the height of the liquid 10 is between adjacent acoustic tubes, the output voltage is constantly maintained during the corresponding interval. Then, as the liquid 10 starts to fill the fourth acoustic tube 30d, the above process is repeated further decreasing the output voltage. It is noted that the acoustic tubes 30a, 30b, 30c, 30d, and 30e may be installed anywhere outside or inside the storage vessel 15.

Figure 4:
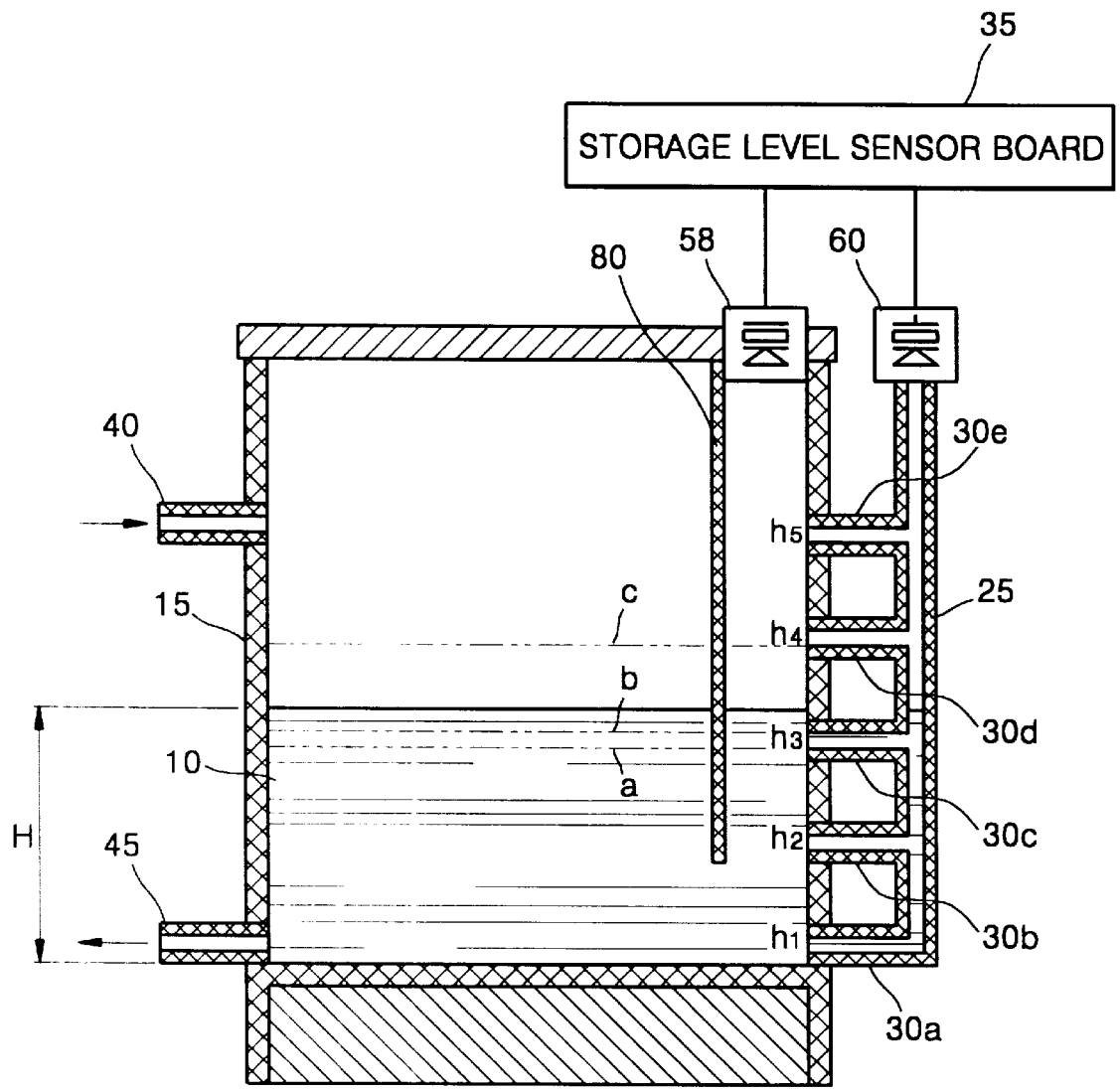
FIG. 4 is a schematic diagram of a liquid level gauge according to another embodiment of the present invention.

FIG. 4 shows the configuration of a liquid level gauge according to another embodiment of the present invention. The speaker 58 is disposed at one top side of the storage vessel 15, and a barrier wall 80 is supported on an upper surface of the vessel and extends downward to enclose the speaker 58 between the wall 80 and the side of vessel 15. The rest of the elements shown in FIG. 4 are the same as the elements of the embodiment shown in FIG. 2.

The barrier wall 80 is disposed adjacent to the acoustic tubes 30a, 30b, 30c, 30d, and 30e, and it does not reach the bottom of the storage vessel 15. That is, the barrier wall 80 is separated from the bottom of the storage vessel 15 by a predetermined height so that the fluid 10 can flow beneath it. If the liquid 10 is circulated by an agitator (not shown), the height of the liquid 10 may increase from the center of the storage vessel 15 toward its wall due to a centrifugal force. Thus, the barrier wall 80 is provided to prevent an inaccurate measurement of a liquid level because the liquid 10 in the space enclosed by the barrier wall 80 is hardly affected by the circulation of the liquid 10. Thus, a more reliable measurement of a liquid level is possible.

Additionally, because the speaker 58 is placed between the wall in which the acoustic tubes 30a, 30b, 30c, 30d, and 30e are disposed and the barrier wall 80, an acoustic wave generated by the speaker 58 is directly transmitted to the acoustic tubes 30a, 30b, 30c, 30d, and 30e. Thus, this increases speed and efficiency of acoustic wave propagation.

Figure 5:
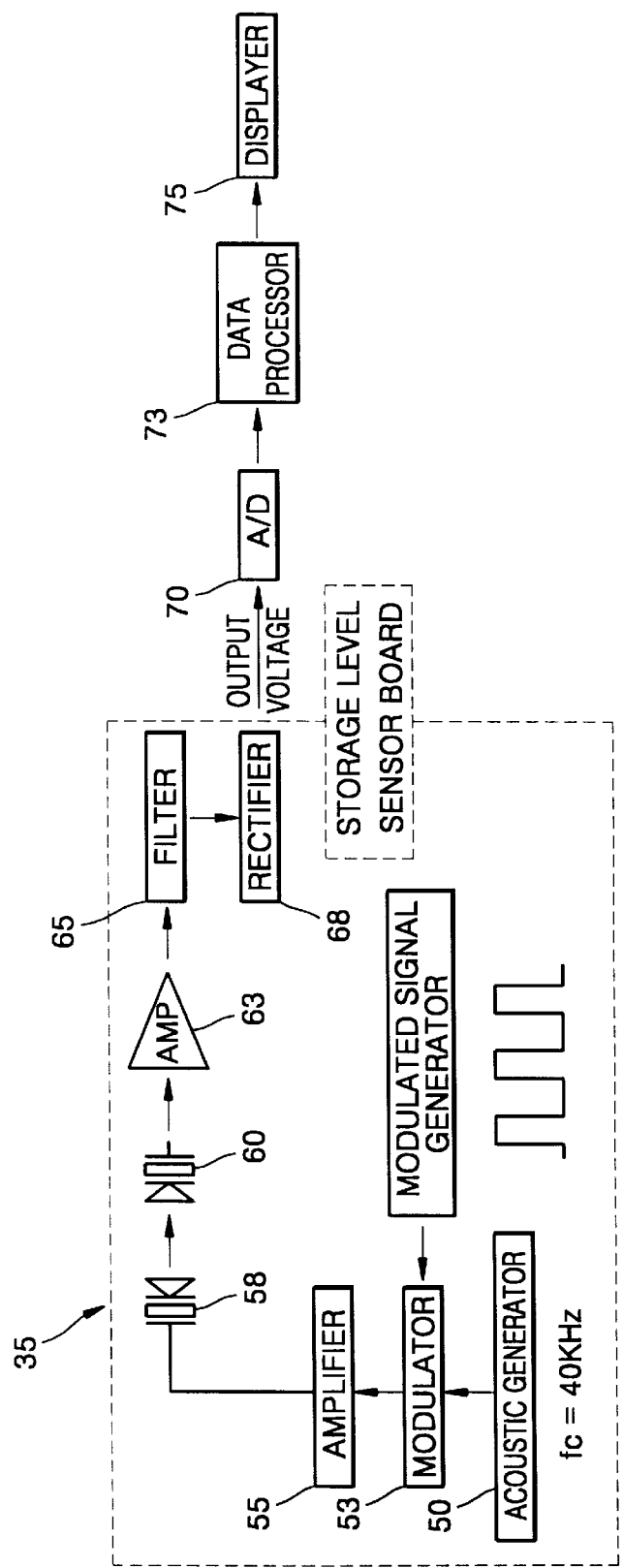
FIG. 5 is a circuit block diagram of a liquid level gauge according to the present invention.

FIG. 5 shows a schematic block diagram of the storage level sensor board 35 used in measuring the storage level of the liquid 10 in the storage vessel 15. Referring to FIG. 5, an acoustic wave generated by an acoustic generator 50 is modulated by a modulator 53 and then amplified by an amplifier 55. Then, the amplified acoustic wave is transmitted through the speaker 58 into the storage vessel 15. Then, the amount of the acoustic wave, which varies depending on the storage level of the liquid 10, is detected by the acoustic sensor 60 and converted into an electrical signal. The electrical signal is amplified by an amplifier 63 and output via a filter 65 and a rectifier 68.

Then, the output voltage is digitalized by an analog-to-digital (A/D) converter 70 and compared with table values by a data processor 73 so as to output the storage level of the liquid 10 in vessel 15. The table values have previously been obtained by experimentation and input to the data processor 73, with each table value corresponding to a specific liquid level. The measured output voltage is compared with the table values to obtain the storage level of the liquid 10 by matching the output voltage to a corresponding table value. The thus-obtained liquid storage level is then displayed through a displayer 75, thereby making it easier to check the level of liquid 10. Although an embodiment of this invention in which the five acoustic tubes 30a, 30b, 30c, 30d, and 30e are disposed has been described, the number of acoustic tubes and their arrangement interval can be appropriately adjusted.

This liquid level measurement can be used to appropriately control the amount of the liquid 10 flowing into or out of the storage vessel 15. Furthermore, this liquid level measurement can be effectively used without restrictions in applied fields.

Next, a method for measuring a liquid level according to the present invention will be described. In the present invention, an acoustic wave is employed so that a liquid level measurement can be made regardless of transparency of the liquid 10. First, an acoustic wave is generated in the storage vessel 15 holding the liquid 10. The acoustic tubes 30a, 30b, 30c, 30d, and 30e opening to the storage vessel 15 are arranged vertically for each storage level of the liquid 10 to be measured, so that the acoustic wave propagates through acoustic tubes located in a part containing no liquid 10 while not significantly propagating through acoustic tubes located in a part filled with the liquid 10. The storage level of the liquid 10 determines which acoustic tubes the acoustic wave propagates through, and the amount of acoustic wave varies depending on the number of acoustic tubes through which the acoustic wave propagates.

The acoustic wave, the amount of which varies depending on the storage level of the liquid 10, is received through the acoustic sensor 60 and output as an electrical signal, or output value. Then, the output value is compared with tabulated reference data to evaluate a corresponding liquid storage level.

The acoustic tubes 30a, 30b, 30c, 30d, and 30e are paths through which an acoustic wave propagates, and an amount of acoustic wave varies depending on the number of the acoustic tubes 30a, 30b, 30c, 30d, and 30e which are above the level of the liquid 10. Thus, simple liquid level measurement is possible using the principle that propagation of an acoustic wave is prevented by the liquid 10.

As described above, the apparatus and method for measuring a liquid level according to the present invention allows a liquid level to be precisely measured, without restrictions on the type of liquid or the range of measurable levels, using an acoustic wave. Furthermore, this invention allows for a precise measurement of liquid level without use of an additional sensor thereby reducing the manufacturing cost.

While the principles of the invention have now been made clear in the illustrated embodiments, it will be readily apparent to one skilled in the art that there are many modifications of structure, arrangements, proportions, the elements, materials, and components used in the practice of this invention and otherwise, which are particularly adapted for specific environments and operation requirements without departing from these principles. The appended claims are therefore intended to cover and embrace any such modifications within the limits only of the true spirit and scope of the invention.

What is claimed is:

1. An apparatus for measuring a liquid level comprising:
   a vessel for receiving a liquid;
   a plurality of acoustic tubes having first ends disposed vertically along a sidewall of the vessel for each liquid level to be measured and communicating with the inside of the vessel, and second ends communicating with a common tube;
   and a storage level sensor board that generates an acoustic wave in the vessel, receives an acoustic wave propagated through one or more of said acoustic tubes and said common tube, and determines the level of the liquid in said vessel based on the received acoustic wave.

2. The apparatus of claim 1, wherein said storage level sensor board comprises:
   an acoustic generator that generates an acoustic wave of predetermined frequency;
   a speaker that transmits the acoustic wave generated by said acoustic generator into said vessel;
   an acoustic sensor that detects the acoustic wave propagated through said one or more of said plurality of acoustic tubes;
   an analog-to-digital converter that digitizes a signal output from said acoustic sensor;
   and a data processor that evaluates a liquid level from data output from said analog-to-digital converter.

3. The apparatus of claim 2, further comprising a display that displays the liquid level evaluated by said data processor.

4. The apparatus of claim 2, further comprising a barrier wall disposed adjacent to said plurality of acoustic tubes, and supported at an upper surface of said vessel, so that said barrier wall is separated from the bottom of said vessel by a predetermined distance.

5. The apparatus of claim 4, wherein said speaker is disposed between said barrier wall and the sidewall of said vessel at which said plurality of acoustic tubes are disposed.

6. The apparatus of claim 2, wherein said speaker is disposed on an upper surface of the inside of said vessel.

7. The apparatus of claim 1, wherein said plurality of acoustic tubes are disposed inside of the vessel.

8. A method of measuring a liquid level, comprising:
   generating an acoustic wave in a vessel for containing a liquid;
   arranging a plurality of acoustic tubes so as to be disposed vertically along a sidewall of the vessel, and receiving an acoustic wave propagated through one or more of the acoustic tubes which are not submerged in the liquid; and
   outputting the received acoustic wave as an electrical signal, comparing the output electrical signal with tabulated data and evaluating a liquid level.

9. The method of claim 8, wherein said generating of the acoustic wave in the vessel comprises:
   generating the acoustic wave at a predetermined frequency using an acoustic generator; and
   transmitting the acoustic wave into the vessel using a speaker.

10. The method of claim 8, wherein said receiving of the acoustic wave comprises detecting the acoustic wave using an acoustic sensor.

11. The method of claim 8, wherein said outputting the received acoustic wave comprises:
    transforming the acoustic wave into an electrical signal using an acoustic sensor;
    converting the electrical signal using an analog-to-digital converter; and
    comparing the converted electrical signal with the tabulated data using a data processor.

12. The method of claim 8, further comprising displaying the liquid level on a display.

13. The method of claim 8, where said generating of the acoustic wave in the vessel comprises transmitting the acoustic wave in an area of the vessel between a barrier wall and the side wall of the vessel.

* * * * *